United States Patent [19]

Birkmayer

[11] Patent Number: 5,444,053

[45] Date of Patent: Aug. 22, 1995

[54] METHOD FOR TREATING SYMPTOMS OF ALZHEIMER'S WITH NADH AND NADPH

[75] Inventor: Joerg G. D. Birkmayer, Vienna, Austria

[73] Assignee: Labor Birkmayer Ges. m.b.H., Vienna, Austria

[21] Appl. No.: 122,035

[22] Filed: Sep. 15, 1993

[30] Foreign Application Priority Data

Sep. 30, 1992 [DE] Germany .................. 42 32 899.3

[51] Int. Cl.⁶ ................ A61K 31/70; A61K 31/455
[52] U.S. Cl. ........................... 514/52; 514/46; 514/356
[58] Field of Search ............ 536/26.24; 514/46, 52, 514/356

[56] References Cited

U.S. PATENT DOCUMENTS

| | | | |
|---|---|---|---|
| 4,814,339 | 3/1989 | Rotondo | 514/332 |
| 4,970,200 | 11/1990 | Birkmayer et al. | 514/52 |
| 5,019,561 | 5/1991 | Birkmayer | 514/52 |

OTHER PUBLICATIONS

Biol. Abstr. No. 90018750, Zubenko et al. J. Neuropathol. Exp. Neurol. 49(3): 206–214, 1990.

*Primary Examiner*—Douglas W. Robinson
*Assistant Examiner*—Gary L. Kunz
*Attorney, Agent, or Firm*—Kenyon & Kenyon

[57] ABSTRACT

A method for improving the cognitive function, memory, and orientation abilities of persons having senile or presenile dementia of the Alzheimer's type wherein the reduced form of nicotinamide-adenine-dinucleotide (NADH), or the reduced form of nicotinamide-adenine-dinucleotide phosphate (NADPH), or physiologically compatible salts of NADH and/or NADPH, are administered orally or parenterally. Patients so treated exhibit greatly improved cognitive abilities over time.

12 Claims, No Drawings

METHOD FOR TREATING SYMPTOMS OF ALZHEIMER'S WITH NADH AND NADPH

BACKGROUND OF THE INVENTION

1. Field of the Invention

The invention relates to a pharmaceutical and a method for treating Alzheimer's Disease, and, more particularly, to the use of reduced forms of nicotinamide-adenine-dinucleotide (NADH), nicotinamide-adenine dinucleotide phosphate (NADPH), and physiologically acceptable salts thereof in the treatment of Alzheimer's disease.

2. Description of Related Art

Alzheimer's disease (i.e., Morbus Alzheimer) can also be described as a presenile dementia of the Alzheimer type (DAT) or, in the nomenclature of modern American psychiatry, as a primary degenerative dementia. It is characterized by the following symptoms: an impairment of cognitive abilities, forgetfulness, confusion, an impairment of short-term and long-term memory, as well as in orientation, and diminished capacity to preserve and care for oneself (i.e., self maintenance and self-care ability). Amyloid deposits, degenerated neurites, as well as proliferating glial cells are found in the brains of Alzheimer patients as elements of senile plaques.

In Alzheimer's patients, a biochemical disruption is found in the neurotransmitter metabolism, particularly of the acetylcholine. A selective loss of cholinergic neurons occurs. In addition, changes in the cell membrane which influence phospholipid conversion have recently been discovered (Petecroof 1989, Annals New York-Academy of Science 586 C, pp. 5–28).

At the present time, there is no substance which alleviates the memory loss and the deterioration of other cognitive abilities experienced by patients with Alzheimer's disease, or which delays the progression or counteracts the development of this disease.

Since acetylcholine is regarded as the critical neurotransmitter for normal cognitive abilities, attempts have been made to influence its synthesis and catalysis in an attempt to counteract the disease. Arencholin, teanol and oxytremorin were tested as cholinomimetic agents on animals. In addition, the acetylcholinesterase inhibitors, etrophonium and tacrine, have been tested on humans in clinical studies. After a double-blind study of both substances, no significant differences could be observed between tacrine and a placebo, as far as ameliorating the symptoms of Alzheimer patients is concerned.

Heretofore, all substances which have been contemplated for treating Alzheimer's disease have not met their expectations in clinical trials. Thus, an enormous need still exists for a medicine to effectively combat and treat Alzheimer's disease.

SUMMARY OF THE INVENTION

Accordingly, it is an object of the invention to provide a new drug and method which is effective in the treatment of Alzheimer's Disease.

In accordance with the invention, the reduced form of nicotinamide-adenine-dinucleotide (NADH), nicotinamide-adenine dinucleotide phosphate (NADPH), or physiologically acceptable salts of NADH/NADPH are administered to Alzheimer's disease patients. Daily single doses of between 1 and 20 mg of NADH may be used for effective treatment. Preferred doses are from 5 to 10 mg in the case of NADH and from 1 to 5 mg in the case of NADPH.

The administration of these endogenous substances as a pharmaceutical leads to surprising therapeutic results, without any side effects. In patients having senile or presenile dementia of the Alzheimer type, a clear improvement in their cognitive function, in their memory, in their orientation ability and their ability to care for themselves is achieved. The intellectual capacity of persons afflicted with Alzheimer's disease improves significantly by 3–4 weeks after treatment with NADH or NADPH.

DETAILED DESCRIPTION OF THE INVENTION

Nicotinamide-adenine-dinucleotide in its reduced form ("NADH") and nicotinamide-adenine-phosphate-dinucleotide in its reduced form ("NADPH") are physiological substances which occur in all living cells including human cells. These substances are cofactors for a variety of enzymes, the majority of which catalyze oxidation-reduction reactions. Prior to recent discoveries as to the therapeutic properties of these compounds, their principal utility has been as diagnostic tools in clinical biochemistry and as essential components in the reaction kits, for example, in measuring Lactatdehydrogenase (LDH).

More recently, NADH and NADPH and pharmaceutically acceptable salts thereof have been shown to be useful in the treatment of Parkinson's Disease. The effectiveness of these agents for this purpose is documented in my existing U.S. Pat. Nos. 4,970,200 and 5,019,561, the disclosure of which are incorporated herein by reference.

However, it was surprising and completely unexpected to discover that these substances are effective in the treatment of Morbus Alzheimer (i.e., Alzheimer's Disease) which is the subject of this application.

When NADH, NADPH, or their physiologically tolerable salts are employed in accordance with the invention, they can be manufactured in the usual way with pharmaceutically acceptable fillers, or they can be incorporated for use as drugs into conventional galenic formulations for oral, parenteral, as well as nasal applications. The preparations can exist: in a solid form as tablets, capsules or coated tablets; in liquid form as a solution, suspension, spray or emulsions, as well as in formulations having a delayed release of active substances.

Suitable oral forms of NADH and NADPH which can be used in the practice of this invention are described in my U.S. Pat. No. 5,332,727, the disclosure of which is incorporated herein by reference. Both NADH and NADPH are very unstable at pHs below 7 which prevail within the confines of the stomach. Therefore, when used in oral form, these substances must be coated with an acid stable protective film so that they can survive the stomach environment for subsequent absorption by the intestine. Suitable acid stable coatings are known in the art and can be applied by a conventional coating process after the active ingredients are formed into a tablet or capsule. Examples of suitable coatings are: cellulose acetate phthalate; polyvinylacetate phthalate; hydroxyl-propyl-methyl cellulose phthalate; metacryllic acid copolymers; fat-wax; shellac; zein; aqua-coating; and surerelease. Another possibility for the coating is a solution of a phthalate and a lack dry substance in isopropanol. An example of a suitable lack dry substance is sold under the name EUDRAGIT ™ by Rohm Pharma. Alternatively, a protein coating in an aqueous medium may be applied. However, a sugar-coating should not be used because it will destabilize NADH.

Although NADH and/or NADPH may be used by themselves in pure form (they are quite stable in compressed form when protected from light), it is preferred that they be combined in a galenic formulation with a stabilizer, and most preferably with both a stabilizer and a filler. It has been found that the following stabilizers are effective and result in the greatest shelf stability for NADH and NADPH: $NaHCO_3$; ascorbic acid and sodium ascorbate; tocopherols and tocopherolacetates; polyvinylpyrolidone ("PVP") 12 (12 representing the molecular weight 12,000); PVP 25; PVP 40; PVP PF 17 (meaning polymer having a molecular weight from 17,000) and PVP PF 60. NADH/NADPH formulations containing such stabilizers are stable for up to two years. Other various stabilizers will become apparent to those skilled in the art.

Suitable fillers for use with NADH and NADPH include: mannitol, microcrystalline cellulose, carboxymethyl cellulose; and dibasic calcium phosphate. Other suitable fillers will become apparent to those skilled in the art. Lactose should be avoided as a filler because it reacts with NADH.

In general, a preferred formulation will include about 3 to 10% by weight NADH and/or NADPH; about 1 to 10% by weight stabilizer; and the remainder as filler. Such a formulation, after being compressed into a pill and coated, is stable for over 24 months.

The NADH and/or NADPH, together with the optional stabilizer and filler, may be formed into tablets, capsules, microtablets or micropellets by processes known in the art of pill manufacturing. Tablets may be formed either by direct compression or by granulation followed by compression. Capsules may be formed by blending the components and subsequently filling capsules with the blend using conventional automatic filling equipment. Microtablets may be formed by compressing powdered or granulated components into, e.g., 2 mm diameter tablets.

In the case of direct compression into tablets, a particularly preferred formulation is: NADH 5%, sodium ascorbate 5%, magnesium stearate 3%, talc 4%, silicon dioxide 1%, and mannitol 82%.

In the case of capsules, a particularly preferred formulation is: NADH 5%, sodium ascorbate 5%, polyvinylpyrolidone (PVP) 5%, microcrystalline cellulose 77%, magnesium stearate 3%, alpha-tocopherolacetate 1% talc 3% and silicon dioxide 1%.

Suitable physiologically acceptable salts of the coenzymes NADH and NADPH include all known physiologically acceptable acidic and basic salt-forming substances, for example: inorganic acids such as, for example, hydrochloric acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

NADH, NADPH or their physiologically compatible salts can be manufactured in the usual manner with pharmaceutically acceptable auxiliaries and carrier materials. If necessary, they can also be used in combination with other active ingredients, for example, postsynaptic dopamine agonists such as Lisuride or Amorphine.

Specific preferred embodiments of the invention will now be described with reference to the following examples which should be regarded in an illustrative, rather than a restrictive, sense.

EXAMPLE 1

A 58 year old female patient had been forgetful for a few years and stated that her condition had deteriorated. She could: no longer find her way back home after going shopping; no longer know what she is supposed to buy; not find her way about in her own house; and not find her way from one room to the next. Her Global Deterioration Score (GDS) was 5, and the result of the Mini-Mental State (MMS) was a score of 8. The patient was diagnosed as having Alzheimer's disease.

The patient was treated by administering 5 mg of NADH daily for one month. After the treatment, a neurological examination revealed that the patient's cognitive abilities had noticeably improved. The patient was able to go shopping; find her way around her home; and watch television and understand the news broadcasts. Objectively, her GDS value decreased to 3, and her MMS value increased to 20. The NADH treatment was subsequently continued and the patient's condition improved somewhat further. No side-effects were observed, nor did the patient complain of any.

EXAMPLE 2

A male patient, 65 years old, had noticed symptoms of forgetfulness and problems with recognition for about six years. A neurological examination revealed: a clearly diminished mental capacity with a GDS value of 5 and an MMS value of 10; problems with his sense of location; a tendency to repeat words; and an inability to read and perform simple arithmetic. Accordingly, the patient was diagnosed with Alzheimer's disease.

After treatment with 5 mg NADH orally, once a day for 36 days, the patient's cognitive functions clearly improved. He could solve simple mathematical problems and had no difficulty finding words. His GDS value was determined to be 3; and his MMS value rose to 22. The treatment was continued for eight weeks and the GDS and MMS values remained essentially unchanged. Subsequently, the treatment was discontinued for one year. After stopping the treatment, there was a renewed deterioration in brain function, and a GDS score of 4 and an MMS value of 16 resulted. Thereafter, a renewed oral NADH treatment (5 mg daily) was begun, resulting in a renewed improvement in brain functions.

EXAMPLE 3

A female patient, 55 years of age, exhibited a severely limited mental capacity. The patient's vocabulary was extremely deficient, she frequently repeated words and exhibited a fixation on certain reiterations. She had great difficulty in reading simple sentences and she failed to understand their meaning. The patient could not perform the simplest of arithmetic tasks and she was unable to count backwards. Her GDS value was 6 and her MMS score was 10, leading to a diagnosis of Alzheimer's disease.

The patient was administered 5 mg NADH daily, orally, for approximately one month. A neurological examination conducted after this treatment showed that her cognitive functions had distinctly improved, her short-term and long-term memory had increased, and that she could perform simple arithmetic and explain the meaning of proverbs. Her GDS value had sunk to 3 and her MMS score had risen to 22. Thereafter, the therapy with NADH was continued by administering 5 mg orally, every second day. The patient's improved condition was maintained and no side effects were observed during this extended therapy.

EXAMPLE 4

A 62 year old male patient was exhibiting distinct forgetfulness and apathy. A neurological examination revealed a strongly limited cognitive capability and impaired temporal and spatial orientation ability. The patient could not state the current date nor recall any recent news. His GDS was 5 and his MMS was 12. Neurologically, he had no organic peculiarities. The patient was diagnosed with Alzheimer's disease.

5 mg of NADPH was administered intravenously, twice a week, for a period of three weeks. After the therapy, the patient exhibited a distinct improvement in his recollection capacity. He could state the correct date and he could recall news which he had heard. His GDS value decreased from 5 to 3 and his MMS score rose from 12 to 25.

EXAMPLE 5

A 57 year old female patient exhibited a seriously limited mental capacity. She was unable to recognize or name objects, and could not repeat words or short sentences. Simple arithmetic (single digit multiplication), as well as reading were not possible, and she had no sense of time or place. She exhibited no neurological or organic peculiarities. Her GDS score was 6 and her MMS value was 4. The patient was diagnosed as having Alzheimer's disease.

2 mg of NADPH was administered intravenously, twice a week, for four weeks. An examination conducted after the therapy revealed that the patient's cognitive abilities had significantly improved. The patient could perform simple arithmetic and draw simple conclusions (by deductive reasoning), and her spatial and temporal orientation ability were significantly improved. Her GDS value had dropped to 4 and her MMS score had risen to 16.

Thereafter, the same four-week long therapy was repeated every second month. The improvement of the patient's condition was maintained during the extended therapy and no side effects were observed. The patient stated that she felt much better physically as well as mentally during the therapy.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A method for improving the cognitive function, memory, and orientation abilities of persons having senile or presenile dementia of the Alzheimer's type comprising the step of administering to a patient suffering from Alzheimer's disease a therapeutic effective amount of NADH or a physiologically compatible salt thereof.

2. The method according to claim 1 wherein the NADH is administered intravenously.

3. The method according to claim 1 wherein the NADH Is administered orally.

4. The method according to claim 1 wherein the NADH is administered in a dose of from 1 mg to 20 mg.

5. The method according to claim 4 wherein the NADH is administered in a dose of from 5 mg to 10 mg.

6. The method according to claim 4 wherein said dose Is administered every 24 hours.

7. The method according to claim 5 wherein said dose is administered every 24 hours.

8. A method for improving the cognitive function, memory, and orientation abilities of persons having senile or presenile dementia of the Alzheimer's type comprising the step of administering to a patient suffering from Alzheimer's disease a therapeutic effective amount of NADPH or a physiologically compatible salt thereof.

9. The method according to claim 8 wherein the NADPH is administered intravenously.

10. The method according to claim 8 wherein the NADPH is administered orally.

11. The method according to claim 8 wherein the NADPH is administered in a dose of from 1 mg to 5 mg.

12. The method according to claim 11 wherein said dose is administered every 24 hours.

* * * * *